(12) United States Patent
Shedd et al.

(10) Patent No.: US 12,343,019 B2
(45) Date of Patent: Jul. 1, 2025

(54) TOURNIQUET WINDLASS ASSEMBLY WITH INTERCHANGEABLE TOOL IMPLEMENTS

(71) Applicant: M-Pak, Inc., Aledo, TX (US)

(72) Inventors: Michael Shedd, Fort Worth, TX (US); Miles Taylor, Aledo, TX (US); Anna Boulware, Aledo, TX (US)

(73) Assignee: M-Pak, Inc., Aledo, TX (US)

( * ) Notice: Subject to any disclaimer, the term of this patent is extended or adjusted under 35 U.S.C. 154(b) by 434 days.

(21) Appl. No.: 18/093,048

(22) Filed: Jan. 4, 2023

(65) Prior Publication Data

US 2023/0233213 A1 Jul. 27, 2023

Related U.S. Application Data

(60) Provisional application No. 63/302,005, filed on Jan. 21, 2022.

(51) Int. Cl.
*A61B 17/132* (2006.01)

(52) U.S. Cl.
CPC ...... *A61B 17/1327* (2013.01); *A61B 17/1325* (2013.01)

(58) Field of Classification Search
CPC .............. A61B 17/132; A61B 17/1322; A61B 2017/00862; A61B 2017/00951
See application file for complete search history.

(56) References Cited

U.S. PATENT DOCUMENTS

2016/0367262 A1 12/2016 Burke et al.

*Primary Examiner* — Ryan J. Severson
(74) *Attorney, Agent, or Firm* — Fulton Jeang PLLC

(57) ABSTRACT

A tourniquet windlass assembly comprises a windlass shaft having an elongated tubular body with an elongated slot defined in the elongated tubular body; at least one end cap removably securable to at least one end of the elongated tubular body of the windlass shaft; a main tourniquet strap; a fastener coupled to the main tourniquet strap and adapted to removably secure and immobilize the windlass shaft relative to the main tourniquet strap; a windlass strap having first and second ends coupled to the main tourniquet strap, and the windlass strap being threaded through the elongated slot defined in the elongated tubular body of the windlass shaft.

20 Claims, 3 Drawing Sheets

TOURNIQUET WINDLASS ASSEMBLY WITH INTERCHANGEABLE TOOL IMPLEMENTS

CROSS REFERENCE TO RELATED APPLICATION

The present application claims the benefit under 35 U.S.C. § 119(e) of U.S. Provisional Application No. 63/302,005 filed on Jan. 21, 2022, the entire disclosure of which is incorporated herein by reference in its entirety.

TECHNICAL FIELD

This disclosure relates to a device for emergency wound treatment, and in particular, a tourniquet windlass assembly with customizable and interchangeable tool implements.

BACKGROUND OF THE DISCLOSURE

A tourniquet is a device that is used in emergency situations to apply pressure to a limb or extremity in order to limit the loss of blood. The tourniquet is generally used to stop or slow the flow of traumatic bleeding, especially by military medics. The tourniquet is usually applied when the patient suffers life-threatening blood loss. Once applied, it is important not to leave the tourniquet in place for too long as that may result in permanent irreversible damage to the patient's limb.

DESCRIPTION OF THE FIGURES

The accompanying drawings facilitate an understanding of the various embodiments.

DETAILED DESCRIPTION

Figure 1:
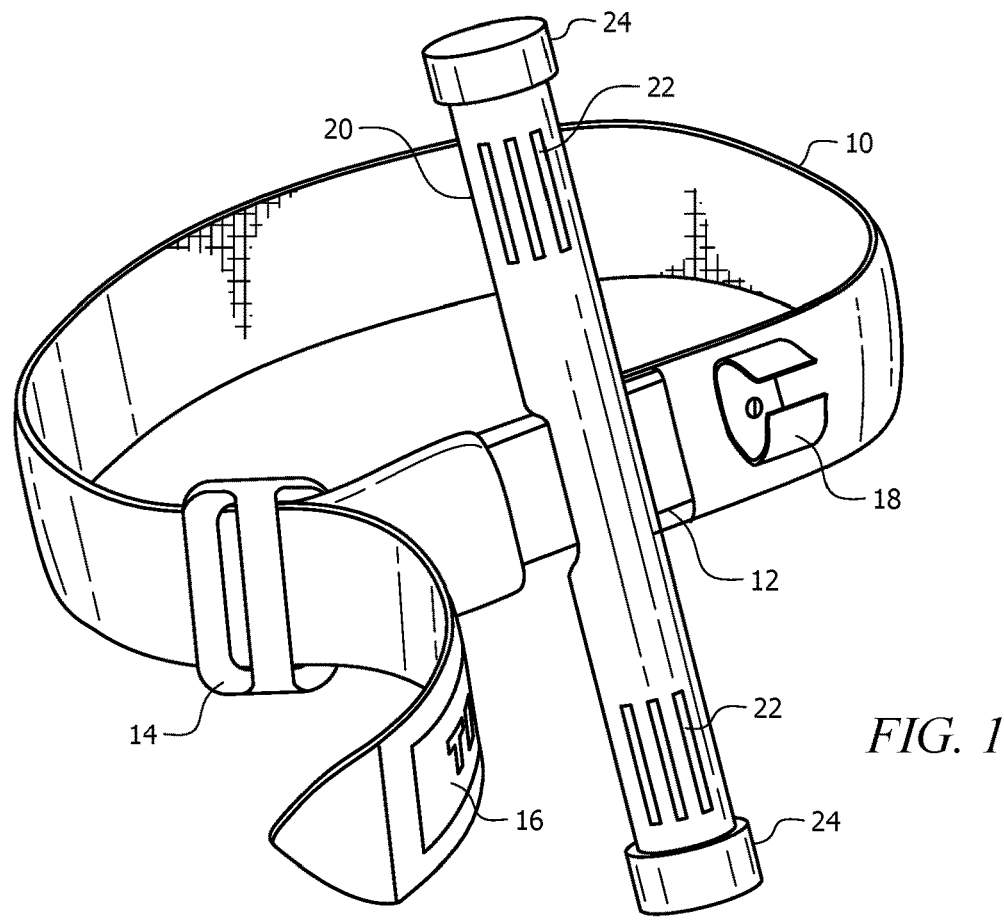
FIGS. 1 and 2 are perspective views of an example embodiment of a tourniquet windlass assembly with customizable and interchangeable tool implements according to the teachings of the present disclosure.
Figure 2:
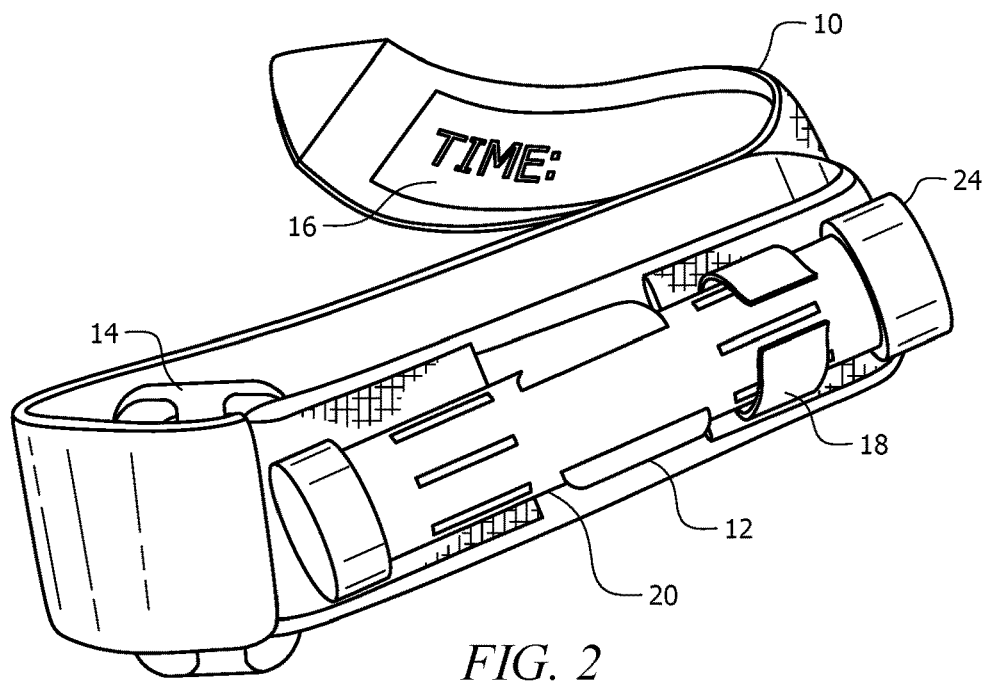
Figure 3:
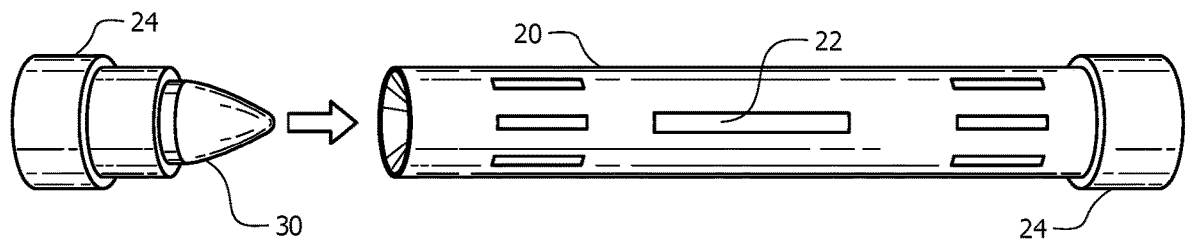
FIG. 3 is a perspective view of an example embodiment of a tourniquet windlass assembly with a writing implement according to the teachings of the present disclosure.
Figure 4A:
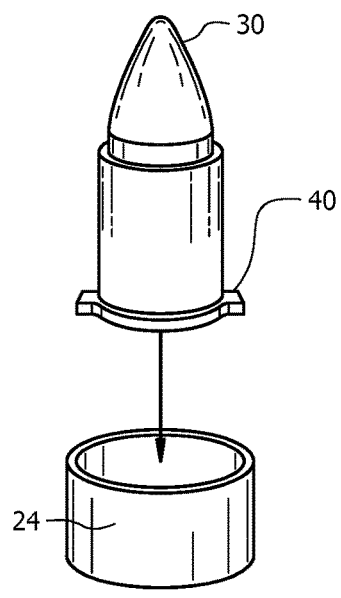
FIGS. 4A-4D are side views of an example embodiment of a tourniquet windlass assembly showing a twist-lock mechanism for securing a writing implement according to the teachings of the present disclosure.
Figure 4B:
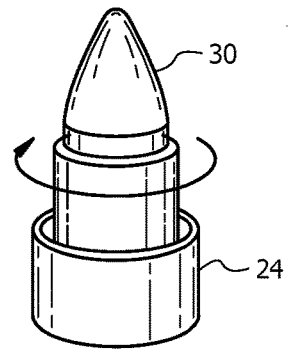
Figure 4C:
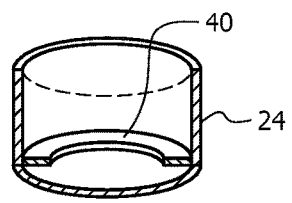
Figure 4D:
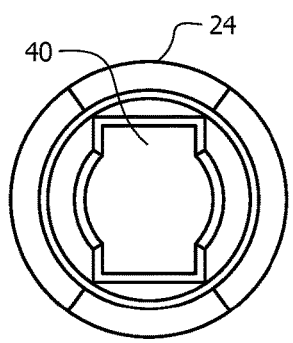
Figure 5A:
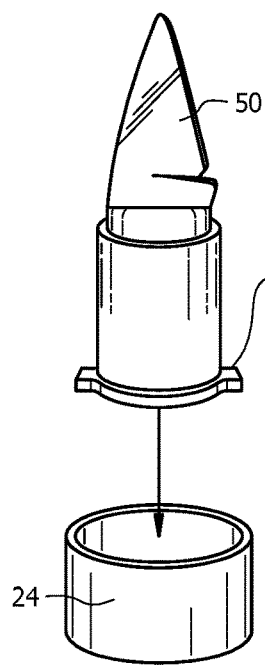
FIGS. 5A and 5B are side views of an example embodiment of a tourniquet windlass assembly showing a twist-lock mechanism for securing a knife implement according to the teachings of the present disclosure.
Figure 5B:
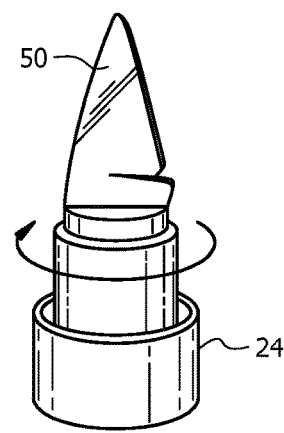
Figure 6A:
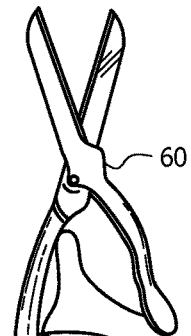
FIGS. 6A and 6B are side views of an example embodiment of a tourniquet windlass assembly showing a twist-lock mechanism for securing a scissors implement according to the teachings of the present disclosure.
Figure 6B:
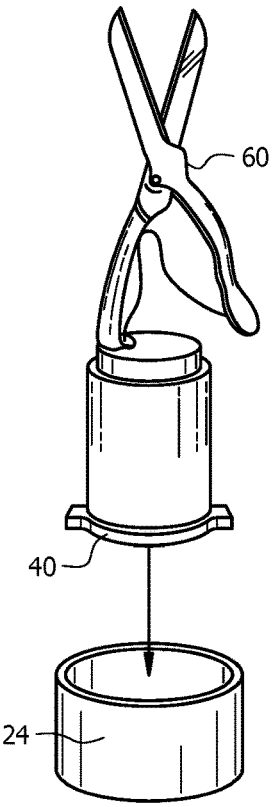
Figure 6B:
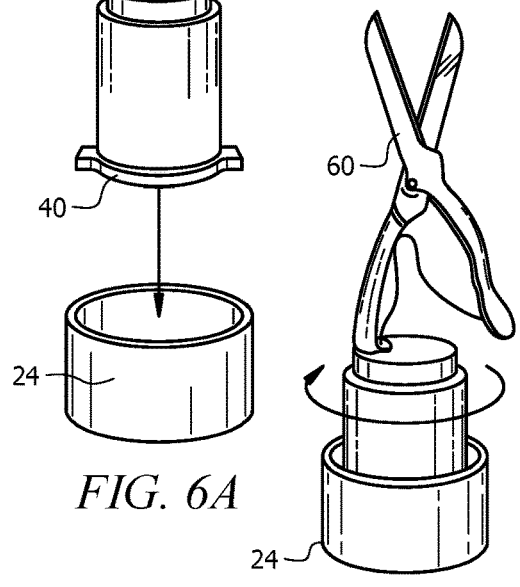
Figure 7A:
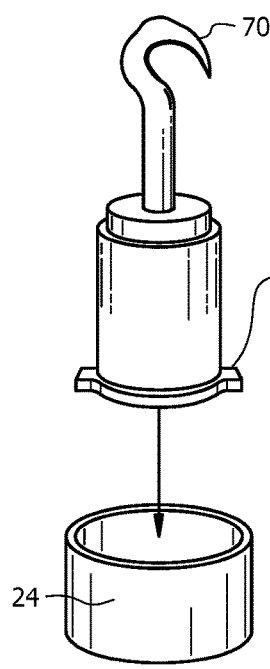
FIGS. 7A and 7B are side views of an example embodiment of a tourniquet windlass assembly showing a twist-lock mechanism for securing a cutter/hook implement according to the teachings of the present disclosure.
Figure 7B:
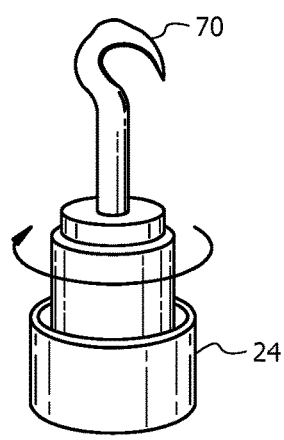

FIGS. 1 and 2 are perspective views of an example embodiment of a tourniquet windlass assembly that incorporates customizable and interchangeable tool implements according to the teachings of the present disclosure. The tourniquet windlass assembly includes a main tourniquet strap or belt attached to a windlass shaft 20. The main tourniquet strap 10 is an elongated strip of flexible material that has sufficient length to extend loosely around a leg or arm of a patient. The main tourniquet strap 10 may be constructed of, for example, a durable woven fabric.

The main tourniquet strap 10 may include a buckle 14 that facilitates tightening and loosening of the main tourniquet strap 10 around the patient's limb. The main tourniquet strap 10 further incorporates a windlass strap 12 coupled to or integrally formed with the main tourniquet strap 10 that is used to secure the windlass shaft 20 to the main tourniquet strap 10. The windlass strap 12 is preferably threaded through an elongated slot defined in the body of the windlass shaft 20 to attach it to the main tourniquet strap 10. As shown in FIG. 2, the windlass strap 12 is flexible and of sufficient length to allow the windlass shaft 20 to rotate with respect to the longitudinal axis of the main tourniquet strap 10 so that it may be secured to the body of the main tourniquet strap 10 using a clip 18 secured to the main tourniquet strap 10. The dimensions and shape of the clip 18 are designed so that its ends latch on to longitudinal grooves 22 formed circumferentially in the windlass shaft 20. The clip 18 and the longitudinal grooves 22 enable the windlass shaft 20 to be securely held and immobilized in an orientation in alignment with the longitudinal axis of the main tourniquet strap 10. The grooves 22 are arranged circumferentially and spaced apart on the exterior wall of the tubular shaft that are consistent with the spatial relationship of the two ends of the clip 18. The clip 18 is designed to making an audible clicking noise when the windlass shaft 20 is pushed into the clip 18 and the clip ends engage the grooves 22.

A reflective label 16 or length of reflective tape with a notation "TIME:" is secured to the main tourniquet strap 10. This label 16 serves as a reminder for the user to note the time when the tourniquet was applied and provides a convenient place to write down the time. This is an important piece of information so that medical personnel may act to avoid permanent damage to the patient's limb.

The windlass shaft 20 has a tubular body constructed of a sturdy and stiff material that provides structural integrity, such as metal, wood, and plastic. The windlass shaft 20 has two removable end caps 24 that are secured to its two ends. The end caps may be secured to the windlass shaft 20 using threaded connection, friction-fit connection, or any other suitable mechanism. As shown in FIGS. 3-7B, the end caps 24 serve as the base for a number of interchangeable and customizable tools and implements, such as a writing tip 30, knife 50, scissors 60, cutter hook 70, etc. These implements may be tools that facilitate the application of the tourniquet (including cutting off the patient's clothing and noting the time of application) or they are capable of other tasks that medical personnel may need. The interior bottom surface of the end cap 24 and the base of each tool implement incorporate female and male components of a twist-lock mechanism that enable a tool implement to be removably engaged to each end cap and enable the tool to be stored within the tubular body of the windlass shaft 20 when not in use. Further, the windlass shaft 20 or end cap 24 may incorporate a light source that can be used to provide general illumination or spotlighting. A light emitting diode or like device may be used for this purpose. The light source may emit light from an exterior surface of the end cap or an exterior surface of the tubular shaft.

In operation, the user may remove the clothing of a patient by using a cutting tool enclosed at one end of the tourniquet shaft by removing an end cap. The user then encircles and properly positions the main tourniquet strap 10 around the patient's bleeding limb. The user may adjust the effective length of the main tourniquet strap 10 around the limb using the buckle 14. The user then releases the windlass shaft 20 from the clip 18 and twists the windlass shaft 20 around its pivot point (the slot) so that the effective length of the main tourniquet strap 10 is shortened and the main tourniquet strap 10 tightens around the limb. The windlass shaft 20, wound around its pivot point, may then be secured to the clip 18 again to maintain the tightened state of the main tourniquet strap 10 around the patient's limb. The audible clicking sound when the windlass shaft 20 is returned to the clip 18 provides added feedback and assurance to the user that the windlass shaft is in the proper position. The user then removes the writing tool attached to another end cap from the windlass shaft and notes the time on the reflective label. The "TIME:" notation on the label serves as an important reminder to the user to write down the time of application.

Although not explicitly shown, other devices or implements may be incorporated. For example, a digital stopwatch may be affixed or fastened to the tourniquet assembly to allow the user to automatically start a time counter to note the lapsed time when the tourniquet has been applied to a patient's limb.

The features of the present invention which are believed to be novel are set forth below with particularity in the appended claims. However, modifications, variations, and changes to the exemplary embodiments described above will be apparent to those skilled in the art, and the tourniquet windlass assembly described herein thus encompasses such modifications, variations, and changes and are not limited to the specific embodiments described herein.

What is claimed is:

1. A tourniquet windlass assembly comprising:
   a windlass shaft having an elongated tubular body with an elongated slot defined in the elongated tubular body;
   at least one end cap removably securable to at least one end of the elongated tubular body of the windlass shaft;
   a main tourniquet strap;
   a fastener coupled to the main tourniquet strap and adapted to removably secure and immobilize the windlass shaft relative to the main tourniquet strap;
   a windlass strap having first and second ends coupled to the main tourniquet strap, and the windlass strap being threaded through the elongated slot defined in the elongated tubular body of the windlass shaft; and
   wherein the fastener is configured to receive and secure the windlass shaft.

2. The tourniquet windlass assembly of claim 1, further comprising at least one tool implement coupled to the at least one end cap, the at least one tool implement being stored within a hollow compartment within the tubular body of the windlass shaft when not in use.

3. The tourniquet windlass assembly of claim 2, wherein the at least one tool implement is removably secured to the at least one end cap by a twist-lock device, the at least one tool implement being selected from the group consisting of a writing implement, a knife, a cutter, a blade, a hook, a light source, and a pair of scissors.

4. The tourniquet windlass assembly of claim 1, further comprising a label secured to the main tourniquet strap for a user to make notes.

5. The tourniquet windlass assembly of claim 1, further comprising a buckle coupled to the main tourniquet strap configured for adjusting the length of the main tourniquet strap around a user's body part.

6. The tourniquet windlass assembly of claim 1, wherein the windlass shaft further comprises circumferentially-arranged elongated grooves about an exterior surface of the tubular body.

7. The tourniquet windlass assembly of claim 1, wherein the fastener comprises a clip, and the windlass shaft further comprises a first series of circumferentially-arranged elongated grooves about an exterior surface of the tubular body near a first end thereof, and a second series of circumferentially-arranged elongated grooves about an exterior surface of the tubular body near a second end thereof, wherein the spatial relationship between adjacent elongated grooves is consistent with the spatial relationship of first and second ends of the clip, and where the first and second ends of the clip make audible clicking sounds against the elongated grooves when the tubular body is pushed into the clip.

8. The tourniquet windlass assembly of claim 1, comprising a timing device coupled to at least one of the main tourniquet strap and tubular body of the windlass shaft.

9. The tourniquet windlass assembly of claim 1, wherein the main tourniquet strap has a sufficient length to allow the windlass shaft to rotate with respect to the longitudinal axis of the main tourniquet strap.

10. The tourniquet windlass assembly of claim 1, wherein the at least one end caps are secured to the ends of the tubular body of the windlass shaft using a connection mechanism selected from the group of threaded connection, friction-fit connection, and twist-lock connection.

11. The tourniquet windlass assembly of claim 1, wherein the elongated tubular body is constructed of a sturdy material.

12. The tourniquet windlass assembly of claim 11, wherein the sturdy material of the tubular body is selected from the group consisting of metal, wood, and plastic.

13. The tourniquet windlass assembly of claim 4, wherein the label comprises a reflective surface.

14. A tourniquet windlass assembly comprising:
    a windlass shaft having an elongated tubular body;
    at least one tool implement coupled to the at least one end of the tubular body, the at least one tool implement being stored within a hollow compartment within the tubular body, the at least one tool implement being selected from the group consisting of a writing implement, a knife, a cutter, a blade, a hook, a light source, a digital timer, and a pair of scissors;
    a main tourniquet strap affixed to a central point of the tubular body of the windlass shaft, the main tourniquet strap having a sufficient length to circumscribe a body part;
    a clip coupled to the main tourniquet strap and adapted to removably secure and immobilize the windlass shaft relative to the main tourniquet strap; and
    wherein the clip is configured to receive and secure the windlass shaft.

15. The tourniquet windlass assembly of claim 14, wherein the at least one tool implement is removably secured to at least one end cap removably secured to at least one end of the tubular body of the windlass shaft.

16. The tourniquet windlass assembly of claim 14, further comprising a reflective label secured to the main tourniquet strap for a user to note the time of tourniquet application.

17. The tourniquet windlass assembly of claim 14, wherein the tubular body of the windlass shaft further comprises circumferentially-arranged elongated grooves about its exterior surface.

18. The tourniquet windlass assembly of claim 14, wherein the windlass shaft further comprises a first series of circumferentially-arranged elongated grooves about an exterior surface of the tubular body near a first end thereof, and a second series of circumferentially-arranged elongated grooves about an exterior surface of the tubular body near a second end thereof, wherein the spatial relationship between adjacent elongated grooves is consistent with the spatial relationship of first and second ends of the clip, and where first and second ends of the clip make audible clicking sounds against the elongated grooves when the tubular body is pushed into the clip.

19. The tourniquet windlass assembly of claim 15, wherein the at least one end caps are secured to the ends of the tubular body of the windlass shaft using a connection mechanism selected from the group of threaded connection, friction-fit connection, and twist-lock connection.

20. A tourniquet windlass assembly comprising:
a windlass shaft having an elongated tubular body with an elongated slot defined in the elongated tubular body;
at least one end cap removably securable to at least one end of the elongated tubular body of the windlass shaft;
a main tourniquet strap;
a C-shaped clip coupled to the main tourniquet strap and adapted to removably secure and hold the tubular body of the windlass shaft relative to the main tourniquet strap;
a windlass strap having first and second ends coupled to the main tourniquet strap, and the windlass strap being threaded through the elongated slot defined in the elongated tubular body of the windlass shaft; and
the windlass shaft further comprises a first series of circumferentially-arranged elongated grooves about an exterior surface of the tubular body near a first end thereof, and a second series of circumferentially-arranged elongated grooves about an exterior surface of the tubular body near a second end thereof, wherein the spatial relationship between adjacent elongated grooves is consistent with the spatial relationship of first and second ends of the clip, and where the clip makes audible clicking sounds against the elongated grooves when the tubular body is pushed into the clip.

\* \* \* \* \*